United States Patent [19]

Dori et al.

[11] Patent Number: 4,866,054

[45] Date of Patent: Sep. 12, 1989

[54] ANTIOXIDANT METALLO-ORGANIC TREATMENT OF INFLAMMATION

[75] Inventors: Zvi Dori; David Gershon, both of Haifa, Israel

[73] Assignee: Chai-Tech Corporation, Greenvale, N.Y.

[21] Appl. No.: 147,713

[22] Filed: Jan. 25, 1988

Related U.S. Application Data

[63] Continuation-in-part of Ser. No. 862,804, May 13, 1986, abandoned.

[51] Int. Cl.$^4$ .................. A61K 31/40; A61K 31/295; A61K 31/555

[52] U.S. Cl. .................................. 514/184; 514/420; 514/501; 514/502

[58] Field of Search ................ 514/184, 420, 501, 502

Primary Examiner—Stanley J. Friedman
Attorney, Agent, or Firm—John P. White

[57] ABSTRACT

A method of treating an inflammatory condition in a mammalian subject, particularly arthritis, comprising the steps of administering an effective and nontoxic dose for an inflammation ameliorating period to the subject of at least one metallo-organic complex capable of in vivo superoxide anti-oxidant effects and wherein the metal of the complex is selected from the group which consists of cobalt and iron.

11 Claims, No Drawings

ANTIOXIDANT METALLO-ORGANIC TREATMENT OF INFLAMMATION

CROSS REFERENCE TO RELATED APPLICATION

This application is a continuation-in-part of Ser. No. 6/862,804, filed May 13, 1986, now abandoned.

FIELD OF THE INVENTION

Our present invention relates to a method of treatment of mammalian subjects for inflammatory conditions and, more particularly, arthritis and like active-oxygen or superoxide based conditions.

BACKGROUND OF THE INVENTION

It has been recognized for some time that inflammation in mammalian species can be traced at least in part to active oxygen species, including superoxide, and radicals associated therewith at the inflammatory site. Considerable research has been undertaken to measure and detect oxygen radicals, to establish the mechanisms whereby enzymes such as superoxide dismutase is effective in countering oxygen radical toxicity and even in the development and use of copper amine oxidases in preventing tissue damage and even in promoting damaged-tissue recovery.

However, the compounds which have been developed heretofore for active-oxygen or superoxide antagonism and destruction in vivo have not proved as effective as desired or were characterized by side reactions or could not be made in commercially significant quantities at reasonable cost.

OBJECTS OF THE INVENTION

It is, therefore, the principal object of our invention to provide an improved method of treatment of mammalian subjects for inflammatory conditions whereby the aforedescribed drawbacks are obviated.

Another object of our invention is to provide an improved method of treating a mammalian subject for a condition resulting from active oxygen or superoxide toxicity which may result in acute or chronic inflammation or any other disorder.

Still another object is to provide a method of treatment which is nontoxic and has no measurable side-effects but which is particularly effective in the treatment of arthritic conditions or the like.

It is also an object to extend the principles of application Ser. No. 06/862,804.

SUMMARY OF THE INVENTION

These objects and others which will become apparent hereinafter are attained, in accordance with the present invention in a method of treating active-oxygen and superoxide associated inflammatory conditions in mammalian subjects which comprises administering an effective and nontoxic dose for an inflammation ameliorating period to the subject of at least one metallo-organic complex capable of in vivo superoxide anti-oxidant effects and wherein the metal of the complex is selected from the group which consists of cobalt and iron.

Preferably the method is used in the treatment of acute or chronic arthritis in a dosage of 0.1 to 250 mg/kg of body weight, but in all cases at most 50% of the $LD_{50}$ value of the compound, when the complex is administered orally as is preferred. However the complex or a combination of the complexes can be administered subcutaneously or even topically in a suitable vehicle, e.g. physiological saline in the case of s.c. administration and dimethylsulfoxide (DMSO) in the case of a topical administration, although ointments, salves or like conventional vehicles may be employed.

For oral administration, the complex or mixture of complexes may be prepared in suitable dosage forms. For example it may be prepared as dragees, as capsules, as tablets, as an elixir or other oral dosage form.

The dose may be administered one to six times daily, depending upon the severity of the inflammatory condition, preferably under medical supervision so that the dosage can be reduced or the number of daily administrations limited as the inflammatory condition subsides.

The compounds of the invention may also have prophylactic properties in preventing the spread of arthritic inflammation and has been found to be effective in reducing the severity of the actual condition which develops in subjects who are prone to such inflammatory states. The compounds may also be effective in preventing postischemic heart damage and for geriatric applications other than as antiarthritics.

We have found that the anti-inflammatory effect is exceptionally pronounced with low-toxicity metallo-organic complexes selected from the group which consists of: [Co{2,3,9,10-tetra{lower-alkyl}-1,4,8,11-tetraazacyclotetra- deca-1,3,8, 10-tetraene}$Cl_2$]Cl, a 1,1-dimethylferrocenium or other alkyl ferrocenium salt, a cobalt(III)-bis(acetyl or propio acetone)-ethylenediimine complex, and [Co{2,12-dimethyl-3,7,11,17-tetraazabicyclo[11.3.1]heptadeca-1(17),2,11,13,15-pentaene}$Cl_2$]Cl·$H_2O$.

In the case of the ferrocenium derivatives, we have discovered that the key to the effect is the ferrocenium ion, so that any physiologically compatible or pharmaceutically effective salt thereof can be employed. Furthermore, the methyl groups are important only in the sense that two methylene structures —$CH_2$—moieties are attached to the ferrocenium moiety. The methyls can thus be substituted by $C_1$ to $C_5$ —alkyl, alkenyl or alkoxy. Best results are obtained with 1-dimethylferrocenium salts.

In the case of the (Co{2, 3, 9,10-tetra{lower-alkyl}-1,4,8, 11-tetraazacyclotetradeca-1,3,8,10-tetraene}$Cl_2$)Cl, we have found that the lower alkyl can be $C_1$ to $C_6$-alkyl but that best results are obtained when the (Co{2,3,9,10-tetra{lower-alkyl}-1,4,8,11-tetraazacyclo tetradeca-1,3,8,10-tetraene}$Cl_2$)Cl is Co{2,3,9,10-tetramethyl-1,4,8,11-tetraazacyclotetradeca-1,3,8,10-tetraene}$C_2$)Cl.

Preferably the cobalt(III)-bis(acetyl or propioacetone)-ethylenediimine complex is a cobalt(III)-bis(acetylacetone)-ethylenediimine complex, and more specifically the [Co(bis{acetylacetone}-ethylenediimine)($NH_3$)$_2$]$^+$$Cl^-$. Alternatively the cobalt(III)-bis(acetyl or propio acetone)-ethylenediimine complex can be the [Co-(bzacen)($NH_3$) $^2$]Cl or Co-B-BEA-64 as described below.

We have found that the complexes specifically identified above can be used together with hitherto-known anti-inflammatories with propionic acid side chains, especially indomethacine, to further alleviate the suffering of arthritic inflammation.

PREPARATION OF THE COMPOUNDS

[Co(Tim)Cl₂]Cl—Compound 8)

Tim=2,3,9,10-tetramethyl-1,4,8,11-tetraazcyclotetradeca-1,3,8,10-tetraene

The procedure of Bush et al (Inorg. Chem., 1972, 11, 2893) was employed to prepare [Co(Tim)Cl₂]PF₆.

A saturated solution of tetramethylammonium chloride in acetone was added slowly to a saturated solution of [Co(Tim)Cl₂]PF₆ in acetone until the solution became cloudy. Cooling afforded light green crystals of compound 8.

Anal Calcd. for $C_{14}H_{24}N_4CoCl_3$: C, 40.63; H, 5.8; N, 13:54. Found: C, 40.57; H, 5.67; N, 13.15.

The compound has the formula:

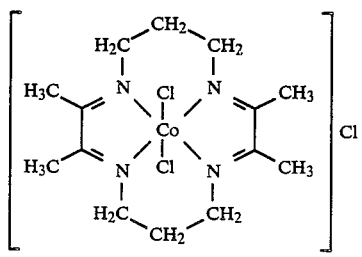

8

1,1-Dimethylferrocenium Salts, (PF₆⁻, Cl⁻, BF₄⁻, Br⁻, ClO₄⁻) - Compound 19)

The procedure of Wahl et al. (J. Phys. Chem., 1975, 79, 2049-52) was employed.

A solution of dimethylferrocene (0.65 g. 3 mmol) in concentrated sulfuric acid (8 ml) was stirred at room temp. for 10 min. and then poured into 60 ml. of cold, dist. water. The insoluble material was removed by filtration, the deep-blue filtrate treated with 0.82 g (5 mmol) of ammonium hexafluorophosphate, stirred for ½ hr. and cooled. The separated solid (compound 19) was collected, washed with ethyl ether and dried under vacuum for two days.

Anal. Calcd. for $C_{12}H_{14}FePF_6$: C, 40.14; H, 3.93. Found: C, 39.98; H, 4.23.

The compound has the formula:

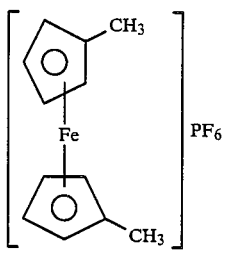

19

Cobalt(III) Bis(acetylacetone)-ethylenediimine Complex (Compound 23)

[Co(BAE)(NH₃)₂]Cl

This complex was prepared by a modification of the procedure described by G. Costa et al., J. Organometal. Chem., 1966, 6, 181-187.

Bis(acetylacetone)-ethylenediimine (BAE, 2.24 g, 10 mmol) was dissolved in methanol (100 ml) and treated with cobalt chloride hexahydrate (2.38 g, 10 mmol). The brown solution was stirred at room temperature for 1½ days in order to allow oxidation of the cobalt (no precipitate formed), treated with 7 ml of conc. aq. ammonia solution, and then heated under reflux for 2 hrs. The yellow-brown solid that separated upon standing was recrystd. from ethanol/water (compound 23).

Anal. Calcd. for $C_{12}H_{24}O_2N_4CoCl$ C, 41.09; H, 6.90. Found: C, 40.81: H, 7.00.

The compound has the formula:

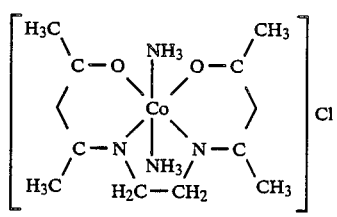

23

[Co(CR)Cl₂]Cl·H₂O (Compound 39)

CR=2,12-dimethyl-3,7,11,17-tetraazabicyclo[11.3.1]heptadeca-1(17),2,11,13,15-pentaene The Co(II) complex, [Co(CR)Cl₂], was prepared and oxidized by the procedure described by Poon et al. for the analogous perchlorate (J. Chem. Soc. Dalton, 1977, 1247-1251). The complex (compound 39) was recrystallized from acetone.

Anal. Calcd. for: $C_{16}H_{24}ON_4CoCl_3$: C, 42.35; H, 5.33; N, 12.35; Cl, 23.45. Found: C, 41.35; H, 5.69; N, 12.07; Cl, 23.64.

The compound had the formula

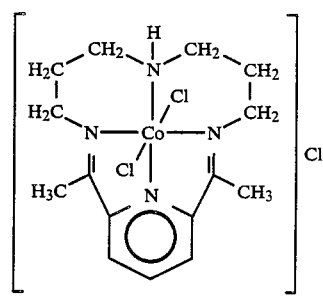

39

N,N'-ethylene bisbenzoylacetone-ethylenediimino-diamminocobalt (III) chloride(Co-bzacen)NH₃) Cl or Co-B-BEA-64) $C_{22}H_{30}N_4O_2CoCl$ (Compound 64)

Preparation of bisbenzoylacetone-ethylendiimine.

To a solution of 0.5 mole of benzoylacetone dissolved acid and filtered, was slowly added with stirring a solution of 0.25 mole of anhydrous ethylenediamine in 10 cc absolute ethanol. The stirring was stopped after the addition of the diamine. The Schiff base was readily obtained after cooling of the solution as white crystals which usually did not require recrystallization.

Preparation of the Co(III) complex.

To 22 mmole of the ligand dissolved in 100 cc of dichloromethane was added a filtered solution of 20 mmole of CoCl₂, 6H₂O in 100 cc absolute methanol. The solution was vigorously stirred in an open vessel while a concentrated solution of ammonium hydroxide was added dropwise. A yellow-ochre product was formed and the product was left overnight. The solution was concentrated in an evaporator and filtered to remove some of the unreacted ligand. Brown needles were obtained after evaporation of the mother liquor. The complex is soluble in ethanol, methanol, water, DMF, dichloromethane etc. . . . The visible absorption spectrum of aqueous solutions exhibits a peak around 300 mm. The N.M.R. and I.R. spectra of the complex are consistent with the expected formula.

The compound had the formula:

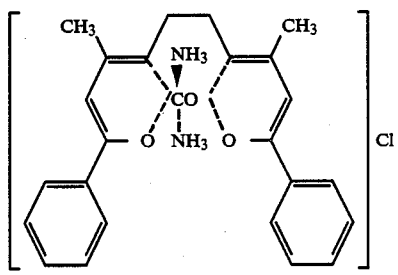

The structure was confirmed by x-ray crystallography.

In vivo Inflammatory Studies

The drugs used are prepared just before performing the experiment. Drugs are dissolved at a concentration of $10^{-2}M$ (or $2\times10^{-2}M$ or $4\times10^{-2}M$) in pyrogen free sterile saline. The dissolved drug is then filtered through a sterile and pyrogen-free 0.2 micron filter (Acrodisc, Gelman).

Procedure

8–12 CD-1 female mice (Charles River), age 2–5 months are numbered, weighed and distributed to 2–3 cages, 3–4 mice in each cage. 0.2 ml of pyrogen-free saline or drug are injected subcutaneously in a randomized order.

Thirty minutes after injecting the drugs or the saline, the right paw of each mouse is injected with 25 microliters of 1% carrageenin (viscarin type, Marine Colloids) in pyrogen-free saline or with 5 microliters (0.227 U) of xanthineoxidase (Sigma).

1.5 hr to 2 hrs after injecting the inflammatory stimulus to the right paw, both paws of the animal are amputated at the knee joint and weighed. The uninjected left paw serves as an internal control for the degree of swelling of the right paw in each animal.

In some experiments the surface temperature of the right and left paws were recorded also before the amputation was performed.

Calculations

The difference in mg between the weight of the right and left paw in control animals (injected with saline) represents 100% of the acute inflammatory response. Concomitantly, the difference between paws of the drug treated animals is calculated and compared to control.

TABLE 1

Effect of several products on carrageenin paw oedema in mice measured by paw weight.

| Product | No. of expts. | total mice | route of admin. | average mg/kg | Paw Weight % activity | % inhibition- |
|---|---|---|---|---|---|---|
| saline | — | — | *S.C. | — | 100% | 0 |
| 23 | 4 | 14 | *S.C. | 25 | 63.1% | 36.9% |
| 8 | 4 | 15 | *S.C. | 29.8 | 73.2% | 26.8% |
| 39 | 5 | 18 | *S.C. | 35.7 | 64.7% | 35.3% |

TABLE 1-continued

Effect of several products on carrageenin paw oedema in mice measured by paw weight.

| Product | No. of expts. | total mice | route of admin. | average mg/kg | Paw Weight % activity | % inhibition- |
|---|---|---|---|---|---|---|
| 19 | 1 | 4 | *S.C. | 23.5 | 88.2% | 11.8% |
| 19 | 3 | 11 | *S.C. | 58.9 | 54% | 46% |

*subcutaneously

TABLE 2

Effect of several products on xanthine-oxidase paw oedema measured by temperature reduction

| Product | No. of expts | total mice | route of admin. | average mg/kg | % activity | % inhibition- |
|---|---|---|---|---|---|---|
| saline | — | — | *S.C. | — | 100% | 0 |
| 23 | 2 | 6 | *S.C. | 22.7 | 31% | 69% |
| 8 | 3 | 10 | *S.C. | 25.1 | 33.2% | 66.8% |
| 19 | 1 | 4 | *S.C. | 46.8 | 69.5% | 30.5% |
| 19 | 3 | 12 | *S.C. | 91.5 | 49.6% | 50.4% |

*subcutaneously

TABLE 3

$LD_{50}$ and $ED_{50}$ of various drugs on xanthine oxidase and carrageenin paw oedema in mice

| | stimulus measurement | :xanthine oxidase :temp. | carrageenin weight mg |
|---|---|---|---|
| Drug | $LD_{50}$ mg/kg | $ED_{50}$ mg/kg | $ED_{50}$ mg/kg |
| 23 | 75 | <38 | 25 |
| 19 | >>875 | 93 | 65 |
| 39 | 85 | — | 43 |
| 8 | 172 | <24 | not determined |

Compound 64 (Co-B-BEA-64) was found to be as effective as or more effective than compound 23 in corresponding tests. All of the compounds were found to be effective in reducing oedema upon oral administration in force feeding with pills containing 8 mg of active ingredient and administered in a quantity sufficient to provide an effective dose. The pills were enterally coated (see below).

Orally and S.C.Administerable Compositions

Example 1

The composition of tablets is as follows:

| | |
|---|---|
| active ingredient (one or more of compounds 8, 19, 23, 39 or 64) | 25.0 mg. |
| corn starch | 97.0 mg. |
| polyvinyl pyrrolidone | 175.0 mg. |
| magnesium stearate | 3.0 mg. |
| | 300.0 mg. |

The active ingredient and the corn starch are wetted by an aqueous polyvinyl pyrrolidone solution of approx. 15% w/v/, followed by granulation, and drying of the wet granules at about 40°–45° C. The dried granulate is thoroughly mixed with magnesium stearate, and the mixture so obtained is further processed by a tablet machine, equipped with an appropriate pressing tool, to give tablets of 300 mg. weight containing 25 mg. of active ingredient. One manufacturing lot includes 1000 tablets.

Example 2

Dragees of the following composition are prepared:

| active ingredient (one or more of compounds 8, 19, 23, 39 or 64) | 50.0 mg. |
|---|---|
| lactose | 94.0 mg. |
| polyvinyl pyrrolidone | 4.0 mg. |
| magnesium stearate | 2.0 mg. |
| | 300 mg. |

Granulates are prepared according to Example 1, and from them dragee kernels of 150 mg. weight are pressed. The dragee kernels are coated with a layer containing sugar and talc followed by coloring with an approved food colorant and polishing with bees wax.

Example 3

25 mg. of active ingredient (one or more of compounds 8, 19, 23 or 39) are dissolved in 1000 ml. of distilled water. The solution is filled into 500 ampoules. In this way ampoules containing 2 ml. of a solution containing 25 mg./ml. of active agent each are obtained. The contents of an ampoule are injected subcutaneously.

Example 4

Gelatin capsules of the following composition are prepared:

| active ingredient (one or more of compounds 8, 19, 23, 39 or 64) | 25.0 mg. |
|---|---|
| maize starch | 122.0 mg. |
| colloidal silica | 3.0 mg. |
| | 150.0 mg. |

The ingredients are homogenized, and the homogenate is filled into hard gelatine capsules. 1000 capsules of 150 mg. (filling) weight each, containing 25.0 mg. of active ingredient per capsule, make a lot.

Example 5

Pills of the active ingredient are enterally coated with a melt of 45 parts of n-butyl stearate, 30 parts of carnauba wax and 25 parts of stearic acid, all by weight, at a temperature of 75° C.

We claim:

1. A method of treating an inflammatory condition in a mammalian subject, comprising the steps of administering an effective and nontoxic dose for an inflammation ameliorating period to said subject of at least one metallo-organic complex capable of in vivo superoxide anti-oxidant effects and is selected from the group which consists of:
   [Co{2,3,9,10-tetra{lower-alkyl}-1,4,8,11-tetraazacyclotetra[deca-1,3,8,10-tetraene}Cl$_2$]Cl, a 1,1-dimethylferrocenium salt, a cobalt(III)-bis(acetyl or propio acetone)-ethylenediimine complex, and [Co{2,12-dimethyl-3,7,11,17-tetraazabicyclo[11.3.1]heptadeca-1(17),2,11,13,15-pentaene)Cl$_2$]Cl·H$_2$O.

2. The method of treating an inflammatory condition in a mammalian subject defined in claim 1 wherein said 1,1-dimethylferrocenium salt is 1,1-dimethylferrocenium hexa-fluorophosphate.

3. The method of treating an inflammatory condition in a mammalian subject defined in claim 1 wherein said [Co{2,3,9,10-tetra{lower-alkyl}-1,4,8,11-tetraazacyclo tetradeca-1,3,8,10-tetraene}Cl$_2$]Cl is [Co{2,3,9,10-tetramethyl-1,4,8,11-tetraazacyclotetradeca-1, 3, 8, 10-tetraene}Cl$_2$]Cl.

4. The method of treating an inflammatory condition in a mammalian subject defined in claim 1 wherein said cobalt(III)-bis(acetyl or propio acetone)-ethylenediimine complex is a cobalt(III)-bis(acetylacetone)-ethylenediimine complex or an N,N'-ethylene-bis(benzoylacetone)-ethylenediimino-cobalt (III) complex.

5. The method defined in claim 4 wherein said complex is N,N'-ethylene-bis(benzoylacetone)-ethylenediiminodiammino-cobalt (III) chloride.

6. The method of treating an inflammatory condition in a mammalian subject defined in claim 1 wherein said cobalt(III)-bis(acetylacetone)-ethylenediimine complex is [Co(bis(acetylacetone}-ethylenediimine)(NH$_3$)$_2$]Cl.

7. The method defined in claim 1 wherein said inflammatory condition is arthritis.

8. The method defined in claim 1 wherein said inflammatory condition is acute arthritis.

9. The method of treating an inflammatory condition in a mammalian subject defined in claim 1 wherein said metallo-organic complex is administered to the subject in combination with a pharmaceutically effective amount of indomethacin.

10. The method of treating an inflammatory condition in a mammalian subject defined in claim 1 wherein said metallo-organic complex is administered to the subject in an oral dosage form.

11. The method of treating an inflammatory condition in a mammalian subject defined in claim 1 wherein said metallo-organic complex is administered to the subject in a topical form.

* * * * *